US012053618B2

(12) United States Patent
Harris et al.

(10) Patent No.: US 12,053,618 B2
(45) Date of Patent: Aug. 6, 2024

(54) FILL-FINISH ASSEMBLIES AND RELATED METHODS

(71) Applicant: AMGEN INC., Thousand Oaks, CA (US)

(72) Inventors: Justin Harris, Reseda, CA (US); Matthew Wayne Janke, Simi Valley, CA (US); Wael Mismar, Redondo Beach, CA (US); Jerome Olivas, Thousand Oaks, CA (US); Thomas Clark Pearson, Newbury Park, CA (US); Sudeshna Dutta Ray, Thousand Oaks, CA (US); Ryan M. Agard, Royersford, PA (US); Alexis Dechelette, Jenkintown, PA (US); Michael Gammelager, Silkeborg (DK); Mads Hansen, Silkeborg (DK); Valerio Mazzon, Padua (IT); Owen Ryan, Wicklow (IE); Clive Smith, Wicklow (IE)

(73) Assignee: AMGEN INC., Thousand Oaks, CA (US)

( * ) Notice: Subject to any disclaimer, the term of this patent is extended or adjusted under 35 U.S.C. 154(b) by 892 days.

(21) Appl. No.: 16/761,149

(22) PCT Filed: Nov. 6, 2018

(86) PCT No.: PCT/US2018/059382
§ 371 (c)(1),
(2) Date: May 1, 2020

(87) PCT Pub. No.: WO2019/090303
PCT Pub. Date: May 9, 2019

(65) Prior Publication Data
US 2020/0338271 A1 Oct. 29, 2020

Related U.S. Application Data

(60) Provisional application No. 62/582,080, filed on Nov. 6, 2017.

(51) Int. Cl.
A61M 5/28 (2006.01)
A61M 5/178 (2006.01)
(Continued)

(52) U.S. Cl.
CPC ............ *A61M 5/28* (2013.01); *A61M 5/1782* (2013.01); *A61M 5/24* (2013.01); *A61M 5/3134* (2013.01);
(Continued)

(58) Field of Classification Search
CPC ........ A61M 5/28; A61M 5/1782; A61M 5/24; A61M 5/3134
See application file for complete search history.

(56) References Cited

U.S. PATENT DOCUMENTS

2013/0237916 A1* 9/2013 Hanson ............... A61M 5/1452
604/151
2015/0231336 A1 8/2015 Edwards et al.

FOREIGN PATENT DOCUMENTS

CA 2991557 A1 1/2017

OTHER PUBLICATIONS

Definition of secure (Year: 2024).*
(Continued)

*Primary Examiner* — Dung T Ulsh
(74) *Attorney, Agent, or Firm* — MARSHALL, GERSTEIN & BORUN LLP; Michael P. Furmanek

(57) ABSTRACT

Fill-finish assemblies facilitating the manufacture of a drug delivery device are disclosed. The fill-finish assembly may include a container, an insertion mechanism, a fluid pathway connection assembly disposed between the container and the insertion mechanism, and a carrier. The insertion mechanism may include a delivery member and an insertion mechanism housing. The insertion mechanism may be configured to move the delivery member from a retracted position inside the insertion mechanism housing to a deployed position outside the insertion mechanism housing. The fluid pathway connection assembly may be selectively activatable to establish fluid communication between the container and the delivery member. The carrier may have a hollow interior containing at least a portion of each of the container, the insertion mechanism, and the fluid pathway connection assembly. The carrier may be configured to hold the container, the insertion mechanism, and the fluid pathway connection assembly in alignment with each other.

9 Claims, 8 Drawing Sheets

(51) Int. Cl.
*A61M 5/24* (2006.01)
*A61M 5/31* (2006.01)
(52) U.S. Cl.
CPC ............... *A61M 2005/2488* (2013.01); *A61M 2005/3115* (2013.01)

(56) References Cited

OTHER PUBLICATIONS

International Search Report for International Application No. PCT/US2018/059382, dated Feb. 13, 2019.
Written Opinion of the International Searching Autthority, for International Application No. PCT/US2018/059382, dated Feb. 13, 2019.

\* cited by examiner

FILL-FINISH ASSEMBLIES AND RELATED METHODS

CROSS-REFERENCE TO RELATED APPLICATION

This is the United States National Phase of PCT/US2018/059382, filed Nov. 6, 2018, which claims the priority benefit of U.S. Provisional Patent Application No. 62/582,080, filed Nov. 6, 2017, the entire contents of each of which are hereby incorporated herein by reference.

FIELD OF DISCLOSURE

The present disclosure generally relates to the manufacture of a drug delivery device and, more particularly, assembling a drug delivery device with a sterile internal fluid flow path.

BACKGROUND

Certain drug delivery devices, including wearable injectors, can be used to assist with the parental delivery of a liquid drug to a patient. Upon activation, certain drug delivery devices will expel a drug stored in an internal reservoir through a needle, cannula, or other delivery member into the patient. Preventing contamination of the drug as it flows internally through the device from the reservoir to the delivery member can be important. Many conventional drug delivery devices are manufactured with an empty reservoir, and the patient or healthcare provider (e.g., a doctor, nurse, healthcare assistant, etc.) would fill the reservoir with the drug at the time of use or treatment. Oftentimes this requires the patient or healthcare provider to operate a syringe to inject the drug into the empty reservoir through an inlet port formed in the exterior of the drug delivery device. Immediately prior to filling, the inlet port may need to be sterilized, for example, by swabbing its outer surface with an alcohol wipe. Certain other conventional drug delivery devices are designed to be installed with a pre-filled drug container by the patient or healthcare provider at the time of use. Before installing the pre-filled drug container, mating connectors disposed on, respectively, the pre-filled drug container and a fluid pathway connection assembly inside the device may need to be sterilized (e.g., by swabbing them with an alcohol wipe). In either case, the drug delivery device may need to be prepared by the patient or healthcare provider prior to use.

To alleviate the patient or healthcare provider of this burden, there is interest in providing a drug delivery device which is pre-loaded or pre-installed with a pre-filled drug container. However, such a device presents several manufacturing challenges, including ensuring that a sterile internal fluid flow path exists between the internal reservoir and the delivery member (e.g., a needle and/or cannula). A conventional drug delivery device which is not pre-loaded with a pre-filled drug container can be subjected to high-energy beams such as x-rays or electron beams at the end of assembly to ensure that its internal components are properly sterilized. Such terminal sterilization may not be feasible for a drug delivery device which is pre-loaded with a pre-filled drug container. This is because the high-energy beams can have deleterious effects on the drug stored in the container. Furthermore, it is sometimes the case that the environment in which the pre-filled drug container and/or other fluid pathway components are installed within the drug delivery device is operated under non-sterile or non-aseptic conditions. Consequently, a risk exists that microbes or other contaminants present in the assembly environment may contaminate the exterior connection surfaces of the drug container and/or other fluid pathway related components.

The present disclosure sets forth assemblies and methods that may address one or more of the challenges or needs mentioned herein, as well as provide other benefits and advantages.

SUMMARY

One aspect of the present disclosure provides a fill-finish assembly including a container, an insertion mechanism, a fluid pathway connection assembly disposed between the container and the insertion mechanism, and a carrier. The insertion mechanism may include a delivery member and an insertion mechanism housing. Additionally, the insertion mechanism may be configured to move the delivery member from a retracted position wherein the delivery member is withdrawn inside the insertion mechanism housing to a deployed position wherein at least a portion of the delivery member extends outside of the insertion mechanism housing. The fluid pathway connection assembly may be selectively activatable to establish fluid communication between the container and the delivery member. The carrier may have a hollow interior containing at least a portion of each of the container, the insertion mechanism, and the fluid pathway connection assembly. Furthermore, the carrier may be configured to hold the container, the insertion mechanism, and the fluid pathway connection assembly in alignment with each other.

Another aspect of the present disclosure provides a method of assembling an insertion mechanism, a fluid pathway connection assembly, and a container for inclusion in a drug delivery device. The method may include: (a) providing a first collar section and a second collar section, each one of the first collar section and the second collar section having a first end and a second end; (b) removably connecting the first collar section to each of the insertion mechanism, the fluid pathway connection assembly, and the container, wherein the fluid pathway connection assembly is disposed between the insertion mechanism and the container; and (c) removably connecting the first end and the second end of the first collar section to, respectively, the first end and the second end of the second collar section to form a carrier having a hollow interior in which at least a portion of each of the insertion mechanism, the fluid pathway connection assembly, and the container is disposed.

Yet another aspect of the present disclosure provides a carrier for holding an insertion mechanism, a fluid pathway connection assembly, and a container while the container is filled with a drug. The carrier may include a first collar section and a second collar section. The first collar section may have a first end and a second end, and the second collar section may have a first end and a second end. The first end and the second end of the second collar section may be removably connectable to, respectively, the first end and the second end of the first collar section to define a hollow interior for receiving at least a portion of each of the insertion mechanism, the fluid pathway connection assembly, and the container. Furthermore, the first collar section and/or the second collar section may be configured to hold the insertion mechanism, the fluid pathway connection assembly, and the container in alignment with each other.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

DETAILED DESCRIPTION

The present disclosure generally concerns manufacturing processes and systems that facilitate the fill-finish processing of one or more components to be included in a pre-loaded and pre-filled drug delivery device. Such drug delivery devices may be manufactured with a sterilized internal fluid flow pathway so that a patient or healthcare provider is not required to sterilize certain element(s) of the drug delivery device prior to use. To provide such a sterilized internal fluid flow pathway, various components or sub-assemblies of the drug delivery device, such as an insertion mechanism and a fluid pathway connection assembly, may be connected to a container and then sterilized prior to filling the container with a drug (also referred to herein as a medicament). This may create a sterilized fluid flow pathway between the container and the insertion mechanism which can later be utilized to safely transfer the drug from the container to the patient during operation of the drug delivery device. In order to maintain the sterility of this fluid flow pathway during subsequent phases of the assembly process, the insertion mechanism, the fluid pathway connection assembly, and the container may remain connected to each other. Consequently, the container may undergo fill-finish processing with the insertion mechanism and the fluid pathway connection assembly connected to the container. The present disclosure describes various processes and assemblies which facilitate this connection, and which temporarily hold the insertion mechanism, the fluid pathway connection assembly, and the container in an arrangement that enables handling and compatibility with certain standard fill-finish equipment and processes.

Figure 1:
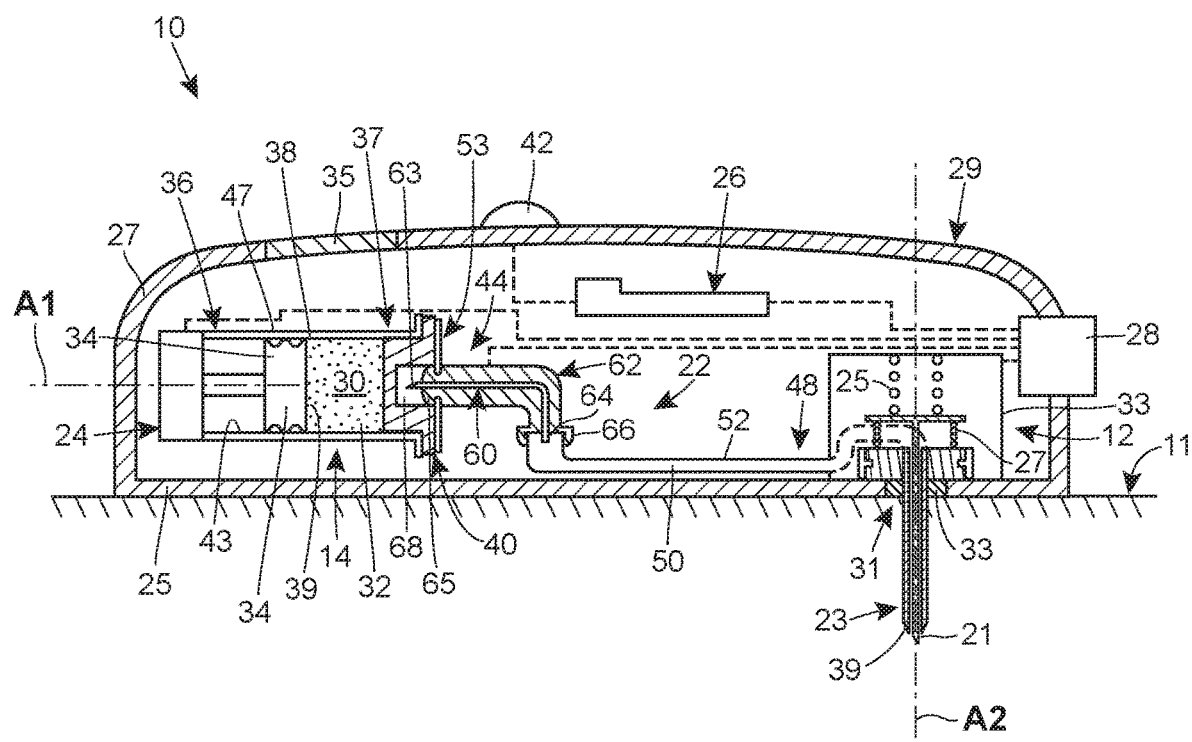
FIG. 1 is a schematic cross-sectional view of an embodiment of a drug delivery device in accordance with principles of the present disclosure.

As a preface to describing the advantageous fill-finish assemblies and related methods of assembly provided by the present disclosure, set forth below in connection with FIG. 1 is a general overview of an embodiment of a drug delivery device 10 which incorporates components whose manufacture is facilitated by the presently disclosed fill-finish assemblies and related methods of assembly. The drug delivery device 10 may be operated to subcutaneously or transdermally deliver a drug to a patient. In the illustrated embodiment, the drug delivery device 10 is configured as a wearable drug delivery device, such as an on-body injector or an ambulatory infusion pump, which is releasably attachable to the patient's tissue 11 (e.g., the patient's skin). In other embodiments (not illustrated), the drug delivery device 10 may be configured as an autoinjector, such as an injection pen, which is temporarily held against the patient's tissue 11 over the course of an injection. The drug delivery device 10 may be configured to automatically deliver a fixed or a patient/operator-settable dose of the drug over a controlled or selected period of time. Furthermore, the drug delivery device 10 may be intended for self-administration by the patient, or may be operated by a formally trained healthcare professional, caregiver, or other user to administer the injection.

Generally, the drug delivery device 10 may include an insertion mechanism 12, a container 14, a fluid pathway connection assembly 22, a drive assembly 24, and a controller 26, each of which may be disposed within an interior enclosed space of a main housing 29. An actuator or input device 28 (e.g., a user-depressible button, touchscreen, microphone, etc.) may protrude through or otherwise be disposed at an exterior surface 19 of the main housing 29 and may be configured to initiate operation of the drug delivery device 10 by activating, via mechanical and/or electrical means (shown in dotted lines in FIG. 1), the insertion mechanism 12, the fluid pathway connection assembly 22, the drive assembly 24, the controller 26, and/or other activatable element(s). In order to activate the insertion mechanism 12, the fluid pathway connection assembly 22, the drive assembly 24, the controller 26, and/or other activatable element(s), the input device 28 may be operably connected to any one of, or any combination of, these elements, directly or indirectly, via mechanical means (e.g., a mechanical linkage or a gear assembly), electrical means, and/or electro-mechanical means. Dotted lines are used in FIG. 1 to schematically illustrate the operational connection between the input device 28 and the insertion mechanism 12, the fluid pathway connection assembly 22, the drive assembly 24, and the controller 26.

Figure 2:
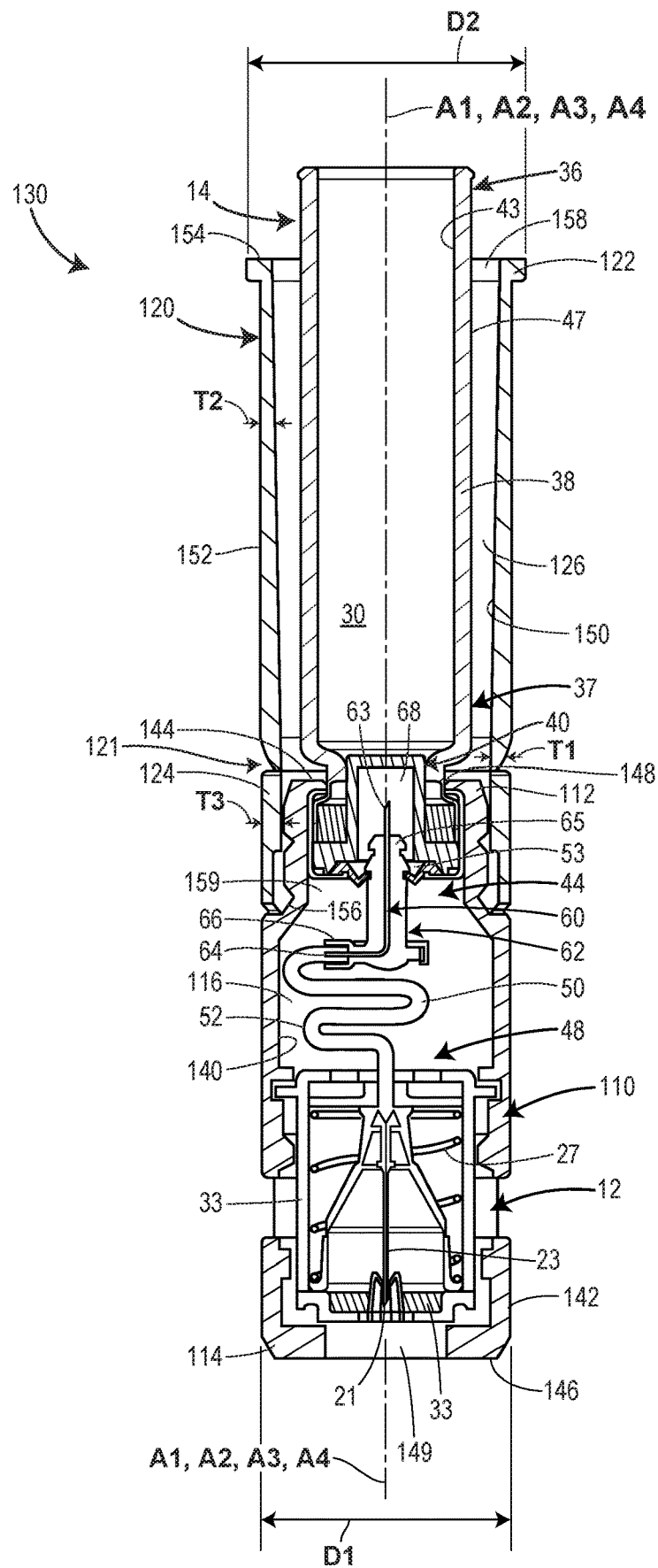
FIG. 2 illustrates a cross-sectional view of an embodiment of a fill-finish assembly in accordance with principles of the present disclosure.

Referring to FIG. 2, the main housing 29 may include a wall 15 having an interior surface 17 and an exterior surface 19. The wall 15 may be a single unitary structure or made of multiple distinct structures interconnected with each other. The interior surface 17 of the wall 15 may define an enclosed space in which the insertion mechanism 12, the container 14, the fluid pathway connection assembly 22, the drive assembly 24, and the controller 26, and/or other mechanisms and/or components may be disposed. In some embodiments, the enclosed spaced may be sealed shut to define an enclosed clean space having, for example, a sterile or aseptic internal atmosphere. The exterior surface 19 of a bottom portion of the wall 15 may be releasably attachable to the patient's tissue 11 (e.g., the patient's skin). In some embodiments, this may be accomplished with a skin adhesive applied to or otherwise disposed at the exterior surface 19 of the bottom portion of the wall 15 of the main housing 29. In some embodiments, the skin adhesive may be part of an adhesive patch attached to the exterior surface 19 of the bottom portion of the wall 15 of the main housing 29. The exterior surface 19 of a top portion of the wall 15 may include one or more visual indicators 42 (e.g., lights, graphical displays, etc.) and/or a window 35 for viewing the container 14 and the drug 32 contained therein. The one or more visual indicators 42 may be used to communicate information to the user about the operational state of the drug delivery device 10 and/or the condition of the drug 32. An opening 31 may be formed in the bottom portion of the wall 15, and optionally a pierceable sterile barrier 33, such as a pierceable septum, may extend across the opening 31 to seal the interior of the main housing 29 prior to use. In some embodiments, the pierceable sterile barrier 33 may be omitted, and instead a removable sealing member (not illustrated) may cover and seal close the opening 31 prior to use.

After the bottom portion of the wall 15 of the main housing 29 is attached to the patient's tissue 13 (e.g., the patient's skin), the insertion mechanism 12 may be activated to move a subcutaneous delivery member from a retracted position, where a pointed distal end of the subcutaneous delivery member is withdrawn inside the main housing 29, to a deployed position, where a pointed distal end projects from the main housing 29 beyond the exterior surface 19 of the main housing 29. In the present embodiment, this may include the insertion mechanism 12 inserting a trocar 21 and a hollow cannula 23 surrounding the trocar 21 through the pierceable sterile barrier 33 and into the patient's tissue 11, as illustrated in FIG. 1. Immediately or shortly thereafter, the insertion mechanism 12 may automatically retract the trocar 21, leaving the distal end of the cannula 23 inside the patient for subcutaneous delivery of the drug 32. The trocar 21 may be solid and have a sharpened end for piercing the patient's skin 11. Furthermore, the trocar 21 may be made of a material that is more rigid than the cannula 23. In some embodiments, the trocar 21 may be made of metal, whereas the cannula 23 may be made of plastic or another polymer. The relative flexibility of the cannula 23 may allow it to be disposed subcutaneously within the patient's tissue 11 for a period of a time without causing pain or significant discomfort to the patient. A distal end 39 of the cannula 23 may be sharpened to a point but may be more blunt than the distal end of the trocar 21. In alternative embodiments (not illustrated), the trocar 21 and cannula 23 may be omitted, and instead the insertion mechanism 12 may insert only a rigid, hollow needle into the patient's tissue 13 for subcutaneous delivery of the drug 32. Also, in any of the above-described embodiments, the subcutaneous delivery member, which may correspond to the cannula 23, may have a longitudinal axis A2 that is perpendicular to or otherwise non-parallel to a longitudinal axis A1 of the container 14 when installed within the drug delivery device 10.

Still referring to FIG. 1, in some embodiments the insertion mechanism 12 may include an insertion mechanism housing 33 enclosing one or both of an insertion biasing member 25 and a retraction biasing member 27. Prior to activation of the insertion mechanism 12, each of the insertion biasing member 25 and the retraction biasing member 27 may be retained in an energized state. Upon activation of the insertion mechanism 12 via, e.g., the input device 28, the insertion biasing member 25 may be allowed to expand or otherwise release its stored energy, thereby moving the subcutaneous delivery member from the retracted position to the deployed position. In the illustrated embodiment, expansion of the insertion biasing member 25 causes the trocar 21 and the cannula 23 to move from their retracted position, where their distal ends are located inside the insertion mechanism housing 33 and/or the main housing 29, to their deployed position shown in FIG. 1, where their distal ends are located outside of the insertion mechanism housing 33 and/or the main housing 29. The retraction biasing member 53 may be retained in its energized state during the insertion procedure. Subsequent to the insertion procedure, the retraction biasing member 53 may release its stored energy and expand to move the trocar 21 from the deployed position back to the retracted position, leaving the cannula 23 in the deployed position.

In the present embodiment, the insertion biasing member 25 and the retraction biasing member 27 are respective compression springs which are arranged concentrically with each other. Other power sources for the insertion biasing member 25 and/or the retraction biasing member 27 are also possible, including, for example, a torsion spring, an electric motor, a hydraulic or pneumatic pump, or a canister that releases a pressurized gas or a pressurized liquid to provide actuation energy. In some embodiments, the insertion biasing member 25 and the retraction biasing member 27 may be defined by a single electric motor which is operated in a forwards and a reverse direction to provide, respectively, the insertion movement and the retraction movement. Also, in some embodiments, the retraction biasing member 27 may be omitted.

With continued reference to FIG. 1, the container 14, which in some contexts may be referred to as a primary container, may include a wall 38 with an interior surface 43 defining a reservoir 30 that is filled with the drug 32 and an exterior surface 47. In some embodiments, as described below in more detail, the reservoir 30 may be pre-filled with the drug 32 by a drug manufacturer prior to installation of the container 14 in the drug delivery device 10. In some embodiments, the container 14 may be rigidly connected to the main housing 29 such that the container 14 cannot move relative to the main housing 29; whereas, in other embodiments, the container 14 may be slidably connected to the main housing 29 such that the container 14 can move relative to the main housing 29 during operation of the drug delivery device 10. The container 14 may have an elongate, barrel-like or cylindrical shape extending along a longitudinal axis A1. In embodiments where the drug delivery device 10 is configured as an on-body injector, the longitudinal axis A1 of the container 14 may be perpendicular or substantially perpendicular, or otherwise non-parallel, to a direction in which the insertion mechanism 12 inserts the subcutaneous delivery member such as the cannula 23 into the patient. This configuration may allow the on-body injector to have a generally planar, low-profile shape that can be worn by the patient without substantially impeding the patient's movement. Initially, a stopper 34 or other piston member may be positioned in the reservoir 30 at a proximal end 36 of the container 14. The stopper 34 may sealingly and slidably engage the interior surface 43 of the wall 38 of the container 14, and may be movable relative to the wall 38 of the container 14 to expel the drug 32 contained therein.

The volume of the drug 32 contained in the reservoir 30 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL, or any volume equal to or greater than approximately (e.g., ±10%) 2 mL, or any volume equal to or greater than approximately (e.g., ±10%) 2.5 mL, or any volume equal to or greater than approximately (e.g., ±10%) 3 mL. The reservoir 30 may be completely or partially filled with the drug 32. The drug 32 may be one or more of the drugs listed below under the heading "Drug Information", such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

During operation of the drug delivery device 10, the drive mechanism 24 may push the stopper 34 along the longitudinal axis A1 from the proximal end 36 of the container 14 to a distal end 37 of the container 14 in order to expel the drug 32 from the container 14. In some embodiments, the drive mechanism 24 may include one or more springs (e.g., coil springs, torsion springs, etc.) initially retained in an energized state, and which are released upon depression of the actuator 28. Following their release, the spring(s) may expand or contract to move the stopper 34 through the reservoir 30 along the longitudinal axis A1 from the proximal end 36 of the container 14 to the distal end 37 of the container 14. In other embodiments, the drive mechanism 24 may include an electric motor (not illustrated) which rotates a gear mechanism, including for example one or more sprocket gears, to cause axial motion of the stopper 34 through the reservoir 30. In still further embodiments, the drive mechanism 24 may include both an electric motor and spring(s), wherein the electric motor regulates expansion of the spring(s) via a tether or pulley system. In still further embodiments, the drive mechanism 24 may include a canister that releases a pressurized gas or pressurized liquid to provide actuation energy.

At the distal end 37 of the container 14, an opening may be formed in the wall 38. At least prior to operation of the drug delivery device 10, the opening may be covered and sealed closed by a seal member 40, such as a pierceable septum, connected to the distal end 37 of the container 14. A proximal end surface of the seal member 40 and the interior surface 43 of the wall 38 of the container 14 may define the reservoir 30. Additionally, in some embodiments, a distal end surface of the stopper 34 may define the reservoir 30.

Generally, the seal member 40 may be configured to selectively permit access to the reservoir 30. During operation of the drug delivery device 10, the seal member 40 may be physically altered (e.g., pierced) to permit fluid communication with the drug 32 in the reservoir 30. In some embodiments, the seal member 40 may be constructed of a flexible or elastically deformable material such as rubber, for example, which is capable of being penetrated or pierced by a sharpened end or point 63 of a container access needle 60 of the fluid pathway connection assembly 22.

In some embodiments, the seal member 40 may be clamped or otherwise secured to the distal end surface of the wall 38 of the container 14 by a fastener (e.g., a crimp ring) and/or adhered directly to the distal end surface of the wall 38 of the container 14.

Still referring to FIG. 1, the fluid pathway connection assembly 22 may be selectively activatable or otherwise configured to establish fluid communication between the container 14 and the insertion mechanism 12 via a sterilized fluid flow pathway during operation or use of the drug delivery device 10. Prior to use of the drug delivery device 10, the fluid pathway connection assembly 22 may not be in fluid communication with the container 14. During setup of the drug delivery device 10, or during the initial stages of operation of the drug delivery device 10 prior to drug delivery, the user may manually, or the drug delivery device 10 may automatically, enable, connect, or open the necessary connections to establish fluid communication between the container 14 and the fluid pathway connection assembly 22. Subsequently, the drive assembly 24 may move the stopper 34 in the distal direction relative to the wall 38 of the container 14 to force the drug 32 stored in the container 14 through the sterilized fluid flow pathway of the fluid pathway connection assembly 22 and into the cannula 23 or needle or other delivery member of the insertion mechanism 12 for subcutaneous delivery to the patient.

In some embodiments, the fluid pathway connection assembly 22 may be rigidly connected to the wall 15 of the main housing 29 such that the fluid pathway connection assembly 22 cannot move relative to the main housing 29; whereas, in other embodiments, the fluid pathway connection assembly 22 may be slidably or moveably connected to the wall 15 of the main housing 29 such that the fluid pathway connection assembly 22 can move relative to the main housing 29 during operation of the drug delivery device 10. In the former embodiments, the container 14 may be slidably or moveably connected to the wall 15 of the main housing 29 such that the seal member 40 can be moved toward and pierced by the point 63 of the stationarily arranged container access needle 60 of the fluid pathway connection assembly 22. In the latter embodiments, the container 14 may be stationarily positioned relative to the main housing 29 while the fluid pathway connection assembly 22 is moved toward the container 14, causing the point 63 of the container access needle 60 to pierce through the seal member 40 and access the reservoir 30.

The fluid pathway connection assembly 22 may include a first end 44 connected to the container 14, a second end 48 connected to the insertion mechanism 12, and a fluid passage 50 extending between the first end 44 and the second end 48. In some embodiments the first end 44 of the fluid pathway connection assembly 22 may be connected to the container 14 via a clip member 53, as shown in FIG. 1. Furthermore, in some embodiments, the first end 44 of the fluid pathway connection assembly 22 may not be in fluid communication with the reservoir 30 of the container 14 until after the drug delivery device 10 and/or the fluid pathway connection assembly 22 has been activated. The second end 46 of the fluid pathway connection assembly 22 may be connected, directly or indirectly, to the subcutaneous delivery member such as the cannula 23. In some embodiments, the second end 46 of the fluid pathway connection assembly 22 may be in fluid communication with an interior of the cannula 23 prior to activation or operation of the drug delivery device 10 and/or the fluid pathway connection assembly 22.

The fluid passage 50 may be sterilized, and may be partially or entirely constructed of a flexible tubing 52. Initially, there may be slack in the flexible tubing 52 to allow the fluid pathway connection assembly 22 to move relative to the housing 29 and/or to allow components of the insertion mechanism 12 to which the fluid pathway connection assembly 22 is attached to move relative to the housing 29.

In some embodiments, the fluid passage 50 may include a rigid fluid restrictor element (not illustrated) in addition to the flexible tubing 52. The fluid restrictor element may have a smaller inner diameter than that of the flexible tubing 52 in order to regulate the flow rate of the drug 32 as it passes through the fluid pathway connection assembly 22. Furthermore, the fluid restrictor element may be made of a more rigid material than the flexible tubing 52. For example, the fluid restrictor element made be made of metal, whereas the flexible tubing 52 may be made of a polymeric material such as plastic. In alternative embodiments, the fluid pathway connection assembly 22 may consist solely of the flexible tubing 52.

Still referring to FIG. 1, the first end 44 of the fluid pathway connection assembly 22 may include the container access needle 60 and an overmold member 62. In general, the overmold member 62 may serve as a mounting member or connection hub for the container access needle 60 and provide a portion of the container access needle 60 which does not access the reservoir 30 with an enlarged outer dimension, such as an enlarged outer diameter. The container access needle 60 may have a sharpened end or point 63, corresponding to a proximal end of the container access needle 60, and a distal end 64 in fluid communication with the fluid passage 50. In the illustrated embodiment, the container access needle 60 has a bend such that the point 63 of the container access needle 60 may be axially aligned with the longitudinal axis A1 of the container 14 whereas the distal end 64 of the container access needle 60 may be perpendicular or otherwise non-parallel to the longitudinal axis A1 of the container 14. The overmold member 62 may cover a length of the container access needle 60, including the bend, with the point 63 of the container access needle 60 protruding outwardly from a proximal end 65 of the overmold member 62. As shown in FIG. 1, a distal end 66 of the overmold member 62 may include a mouth or opening that allows an end of the flexible tubing 52 to be inserted into the overmold member 62. In alternative embodiments, the distal end 66 of the overmold member 62 may be inserted into an opening formed in the end of the flexible tubing 52.

The container access needle 60 may possess a hollow, tubular shape with one or more openings formed at each of the point 63 and/or the distal end 64. The container access needle 60 made be constructed of a rigid material including, but not limited to, metal (e.g., stainless steel) and/or plastic. In some embodiments, the overmold member 62 may be constructed of a different material than the container access needle 60 such that the overmold member 62 and the container access needle 60 are separate, but rigidly connected, components. In some embodiments, the overmold member 62 may be constructed of a rigid plastic material whereas the container access needle 60 is constructed of metal. In other embodiments, the overmold member 62 and the container access needle 60 may be made of the same material and integrally formed such that they form a single, unitary one-piece structure.

In some embodiments, displacing the input device 28 may cause the simultaneous or substantially simultaneous activation of the insertion mechanism 12, the fluid pathway assembly 22, the drive assembly 24, the controller 26, and other activatable element(s) of the drug delivery device 10, or any combination thereof. In other embodiments, displacing the input device 28 may cause the insertion mechanism 12, the fluid pathway assembly 22, the drive assembly 24, the controller 26, and other activatable element(s) to activate in a predetermined sequential order.

Where appropriate, any of the above-described sub-assemblies, mechanisms, components, features, functionalities, methods of assembly or manufacture, methods of use, and other aspects of the drug delivery device 10 may be replaced with and/or combined with any of the sub-assemblies, mechanisms, components, features, functionalities, methods of manufacture or assembly, methods of use, and other aspects of the drug delivery devices described in some or all of the following documents, each of which is hereby incorporated by reference in its entirety for all purposes: U.S. Pat. Nos. 9,061,097; U.S. Patent Application Publication No. 2017/0124284; U.S. Patent Application Publication No. 2017/0119969; U.S. Patent Application Publication No. 2017/0098058; U.S. Patent Application Publication No. 2017/0124285; U.S. Patent Application Publication No. 2017/0103186; U.S. Provisional Patent Application No. 62/460,501 entitled "INSERTION MECHANISM FOR DRUG DELIVERY DEVICE"; U.S. Provisional Patent Application No. 62/469,226 entitled "INSERTION MECHANISM FOR DRUG DELIVERY DEVICE"; U.S. Provisional Patent Application No. 62/468,190 entitled "INSERTION MECHANISM AND METHOD OF INSERTING A NEEDLE OF A DRUG DELIVERY DEVICE"; U.S. Provisional Patent Application No. 62/460,559 entitled "DRUG DELIVERY DEVICE WITH STERILE FLUID FLOWPATH AND RELATED METHOD OF ASSEMBLY"; U.S. Provisional Patent Application No. 62/294,842 entitled "DRUG DELIVERY DEVICE, METHOD OF MANUFACTURE, AND METHOD OF USE"; U.S. Provisional Patent Application No. 62/297,718 entitled "DRUG DELIVERY DEVICE, METHOD OF MANUFACTURE, AND METHOD OF USE"; U.S. Provisional Patent Application No. 62/320,438 entitled "DRUG DELIVERY DEVICE, METHOD OF MANUFACTURE, AND METHOD OF USE"; U.S. Provisional Patent Application No. 62/535,777 entitled "GAS PERMEABLE SEALING MEMBER FOR DRUG CONTAINER AND METHODS OF ASSEMBLY"; U.S. Provisional Patent Application No. 62/536,909 entitled "DRUG DELIVERY DEVICE WITH CONTAINER ACCESS SYSTEM AND RELATED METHOD OF ASSEMBLY"; U.S. Provisional Patent Application No. 62/536,911 entitled "DRUG DELIVERY DEVICE WITH GEAR MODULE AND RELATED METHOD OF ASSEMBLY"; U.S. Provisional Patent Application No. 62/547,500 entitled "WEARABLE INJECTOR WITH STERILE ADHESIVE PATCH"; U.S. Provisional Patent Application No. 62/548,750 entitled "NEEDLE INSERTION MECHANISM FOR DRUG DELIVERY DEVICE"; U.S. Provisional Patent Application No. 62/569,999 entitled "DRUG DELIVERY DEVICE WITH DRIVE ASSEMBLY AND RELATED METHOD OF ASSEMBLY"; International Patent Application No. PCT/US2017/017627 entitled "DRUG DELIVERY DEVICE, METHOD OF MANUFACTURE, AND METHOD OF USE"; International Patent Application No. PCT/US2017/026524 entitled "DRUG DELIVERY DEVICE, METHOD OF MANUFACTURE, AND METHOD OF USE"; International Patent Application Publication No. WO/2016/130679 entitled "ROTATIONALLY BIASED INSERTION MECHANISM FOR A DRUG DELIVERY PUMP"; International Patent Application Publication No. WO/2016/141082 entitled "DEVICE AND METHOD FOR MAKING ASEPTIC CONNECTIONS"; and International Patent Application Publication No. WO/2016/145094 entitled "DRIVE MECHANISMS FOR DRUG DELIVERY PUMPS".

Methods of assembling the drug delivery device 10 and its various components and subassemblies will now be described. Various phases of the assembly process may be performed in different facilities or environments having different levels of cleanliness (e.g., different cleanroom classifications). Some assembly environments may be operated under sterile or nearly sterile conditions, whereas other assembly environments may be operated under aseptic, or even non-aseptic, conditions. In certain situations, it may not be practical or economically feasible to operate each and every assembly environment under sterile conditions. Furthermore, transferring the components or subassemblies between the different assembly environments may expose them to non-sterile or non-aseptic conditions. As a result, certain manufacturing techniques may be needed to ensure that the drug delivery device 10 is assembled with a sterilized internal fluid flow pathway that can be accessed during operation of the drug delivery device 10 in order to establish fluid communication between the container 14 and the cannula 23 or other delivery member of the insertion mechanism 12 and thereafter safely delivery the drug 32 to the patient without requiring the patient or a healthcare provider to sterilize fluid flow pathway related components of the drug delivery device 10 prior to use.

An initial phase of the assembly process may involve connecting the container 14, the fluid pathway connection assembly 22, and the insertion mechanism 12. During this phase, the reservoir 30 of the container 14 may be empty. The method may involve covering the opening at the distal end 37 of the container 14 with the seal member 40, such that a proximally facing end surface of the seal member 40 directly contacts a distally facing end surface of the container 14. Next, the clip member 53 may be disposed on the seal member 40, such that a proximally facing end surface of the clip member 53 directly contacts a distally facing end surface the seal member 40. Next, a fastener such as a crimp ring may be applied to an exterior surface clip member 53 and the exterior surface 47 of the wall 38 of the container 14 to secure the clip member 53 and the container 14 with the seal member 40 positioned between the clip member 53 to the container 14. A clamping force provided by the fastener may form of a fluid-tight and/or air-tight seal between the proximally facing end surface of the seal member 40 and the distally facing end surface of the container 14 and/or between the distally facing end surface of the seal member 40 and the proximally facing end surface of the clip member 53. In some embodiments, during the present phase, the assembled arrangement of the empty container 14, the seal member 40, the clip member 53, and the crimp ring may be subjected to radiation sterilization (e.g., x-ray radiation, gamma ray radiation, and/or electron beam radiation) in order to sterilize the interface between the seal member 40 and the container 14.

Next, the first end 44 of the fluid pathway connection assembly 22 may be connected to the container 14, but without establishing fluid communication between the reservoir 30 of the container 14 and the fluid pathway connection assembly 22. This step may involve inserting the proximal end 65 of the overmold member 62 through a hole in the clip member 53 and into a recess formed in the seal member 40. As a result, the point 63 of the container access needle 60 may be either disposed in an enclosed clean space 68 between the seal member 40 and the overmold member 62 or embedded within the material of the seal member 40.

Subsequently, the second end 48 of the fluid pathway connection assembly 22 may be connected to the insertion mechanism 12, with or without establishing fluid communication between the fluid passage 50 and the cannula 23 or other delivery member of the insertion mechanism 12. The insertion mechanism 12 may be completely or partially assembled prior to this step.

Next, the empty container 14, the fluid pathway connection assembly 22, and the insertion mechanism 12 may be secured or otherwise stationarily positioned relative to each other in a configuration or formation that facilitates downstream handling of the arrangement by certain standard fill-finish equipment. Such equipment may be designed to handle containers or syringes having an elongate barrel-like or cylindrical shape. To mimic or replicate this shape in at least some respects, the empty container 14, the fluid pathway connection assembly 22, and/or the insertion mechanism 12 may be temporarily held in alignment with each other by a carrier 110, as shown in FIG. 2. This may involve removably connecting the carrier 110 to each of, or any combination of, the empty container 14, the fluid pathway connection assembly 22, and the insertion mechanism 12. In some embodiments, bracing the empty container 14, the fluid pathway connection assembly 22, and/or the insertion mechanism 12 with the carrier 110 may orient the longitudinal axis A1 of the container 14 such that it is parallel, or otherwise non-perpendicular, to and/or coaxial with the longitudinal axis A2 of the cannula 23 or other delivery member of the insertion mechanism 12. In some configurations, the longitudinal axis A1 of the container 14 and/or the longitudinal axis A2 of the cannula 23 may be parallel, or otherwise non-perpendicular, to and/or coaxial with a longitudinal axis A3 of the carrier 110. The configuration of the carrier 110 and its connection to the container 14, the fluid pathway connection assembly 22, and/or the insertion mechanism 12 will be described in more detail below.

Optionally, the proximal end 36 of the container 14 may be inserted into a hollow interior 126 of a sleeve 120. The sleeve 120 may be slid over the container 14 and then removably connected to a proximal end of the carrier 110. One of the functions of the sleeve 120 may be to cover and/or protect the container 14 during the drug filling process. As described below in more detail, the sleeve 120 may have a parting line 121 allowing a proximal end 122 of the sleeve 120 surrounding the container 14 to be removed from a distal end 124 of sleeve 120 which is connected to the carrier 110 after the container 14 has been filled with the drug 32. Removal of the proximal end 122 of the sleeve 120 may allow the drug 32 to be visually inspected for particulates and other quality or safety assurance measures once filling is complete. In alternative embodiments, the parting line 121 may be omitted and the sleeve 120 may be made of a transparent material such that the drug 32 in the container 14 can be inspected without having to remove the portion of the sleeve 120 covering the body of the container 14.

The assembled arrangement of the container 14, the fluid pathway connection assembly 22, and the insertion mechanism 12, the carrier 110, and optionally the sleeve 120 may be referred to as a fill-finish assembly 130. Subsequently, the fill-finish assembly 130 may be subjected to a sterilization treatment, including, but not limited to, radiation sterilization treatments (utilizing, e.g., gamma rays, x-rays, and/or electron beams) and/or gaseous sterilization treatments (utilizing, e.g., ethylene oxide, ozone, chlorine dioxide, nitrogen dioxide, and/or steam). This sterilization treatment may create a sterilized fluid flow pathway between the container 14 and the delivery member of insertion mechanism 12.

Next, the fill-finish assembly 130 may be enclosed within a package having a sterile internal atmosphere, or other medical grade packaging, and then shipped or otherwise transferred to a fill-finish facility. In some implementations, the above-described steps of assembling the fill-finish assembly 130 may be performed in a facility operated by a medical device manufacturer, whereas the below-described steps related to fill-finish processing may be performed in a facility operated by a pharmaceutical or drug manufacturer. During this transfer between facilities, the fill-finish assembly 130 may be protected from contamination by virtue of being enclosed within the package.

Subsequently, for example, at a facility operated by a drug manufacturer, the fill-finish assembly 130 may be removed from the package and the reservoir 30 of the container 14 may be filled with the drug 32. Also, the stopper 34 may be inserted into the reservoir 30 to seal close the opening in the proximal end 36 of the container 14. During these steps, the carrier 110 may remain attached to the container 14, the fluid pathway connection assembly 22, and/or the insertion mechanism 12 in order to keep these elements linearly aligned with each other. Advantageously, this may allow for the fill-finish assembly 130 to be handled by certain standard fill-finish equipment and/or processes. Accordingly, the drug manufacturer may not be required to replace its existing fill-finish equipment, or at least not make extensive modifications to its existing fill-finish equipment, in order to accommodate the filling of the container 14, which is to be later installed in the drug delivery device 10. Furthermore, in some embodiments, because of its elongate and generally linear shape, the fill-finish assembly 130 may be carried by a tray together with a plurality of other fill-finish assemblies 130. Such a tray may have a plurality of wells, each of which receives a corresponding one of the fill-finish assemblies 130 and which orient the fill-finish assemblies 130 such that the longitudinal axes A1 of the containers 14 are parallel to each other. A distal end of the fill-finish assembly 130 may be inserted into a respective one of the wells such that the proximal end 36 of the container 14 is exposed at the top of the tray and can be filled with a drug 32 which is dispensed from above. Also, in some embodiments, the fill-finish assembly 130 may be shipped together with other fill-finish assemblies 130 in such a tray from the initial manufacturing facility to the fill-finish facility, with the tray and its contents being enclosed within medical grade packaging.

In some embodiments, the fill-finish processing may be conducted under sterile or aseptic conditions such that the previously-established sterile fluid flow pathway between the container 14 and the delivery member of the insertion mechanism 12 is not compromised. Also, because the fluid flow pathway between the container 14 and the delivery member of the insertion mechanism 12 has already been sterilized, it may not be necessary to subject the arrangement to a radiation sterilization treatment, which could result in molecular damage to the drug 32 in the container 14. Also, once the container 14 has been filled and capped with the stopper 34, the container 14, the fluid pathway connection assembly 22, and the insertion mechanism 12 may define a self-contained and/or sealed unit which can be handled in non-sterile environments (including, e.g., a final assembly environment where all components of the drug delivery device 10 are combined) with little or no risk of microbial contamination of the fluid flow pathway between the container 14 and the delivery member of the insertion mechanism 12. Nevertheless, in some embodiments, after filling and capping is complete, the fill-finish assembly 130 may be subjected to a gaseous sterilization treatment (utilizing, e.g., ethylene oxide, ozone, chlorine dioxide, nitrogen dioxide, and/or steam) to eliminate or reduce contaminants on exterior surfaces of the arrangement.

Next, the proximal end 122 of the sleeve 120 may be detached from the distal end 124 of the sleeve 120 at the parting line 121 in order to uncover the container 14. This may allow the drug 32 stored in the container 14 to be visually inspected, manually or automatically, for particulates, bubbles, color, and/or to confirm other quality or safety assurance measures. The detachment may involve ripping, tearing, breaking, cutting, or otherwise physically separating the sleeve 120 at the parting line 121 such that the sleeve 120, which was previously made of a single unitary, one-piece structure, is divided into two or more pieces. The carrier 110 may remain connected to the insertion mechanism 12, the container 14, and the fluid pathway connection assembly 22 during removal of the proximal end 122 of the sleeve 120. In some embodiments, the proximal end 122 of the sleeve 120 may be removed by pulling it in a direction that is parallel to the longitudinal axis A3 of the carrier 110. The distal end 124 of the sleeve 120 may stay connected to the carrier 110 during and after removal of the proximal end 122 of the sleeve 120.

In some embodiments, prior to or during the visual inspection of the drug 32, the fill-finish assembly 130 may be spun in a centrifuge and/or agitated in order to isolate or separate particulates or other undesirable elements from the drug 32. These procedures as well as other handling, conveying, or transferring of the fill-finish assembly 130 may subject the fill-finish assembly 130 to significant inertial forces. To prevent or inhibit the insertion mechanism 12, the container 14, and/or the fluid pathway connection assembly 22 from rotating or moving axially relative to each other and/or the carrier 110 during such inertial maneuvers, the carrier 110 may include various gripping elements to resist movement of the insertion mechanism 12, the container 14, and/or the fluid pathway connection assembly 22, as described below in more detail. Advantageously, this may reduce the possibility of flexible components, such as the flexible tubing 52 of the fluid pathway connection assembly 22, from being twisted or stretched during the fill-finish procedures and/or other handling.

Next, the fill-finish assembly 130 may be shipped or transferred to a facility where the final assembly of the drug delivery device 10 is to occur. In some embodiments, the fill-finish assembly 130 may be shipped or transferred to the final assembly facility in a tray, such as the one described above, together with a plurality of other fill-finish assemblies 130. At the final assembly facility, the carrier 110 may be removed or detached from the insertion mechanism 12, the drug-filled container 14, and the fluid pathway connection assembly 22, thereby allowing these components to be re-arranged relative to each other. The distal end 124 of the sleeve 120 may also be detached at this stage if it has not been done so already. Subsequently, the insertion mechanism 12, the drug-filled container 14, and the fluid pathway connection assembly 22 may be installed within the housing 29 of the drug delivery device 10 together with other components and/or sub-assemblies of the drug delivery device 10. After being installed within the drug delivery device 10, the longitudinal axis A1 of the container 14 may be perpendicular or otherwise non-parallel to the longitudinal axis A2 of the delivery member of the insertion mechanism 12.

In some embodiments, the final assembly of the drug delivery device 10 may be carried out in a non-sterile or non-aseptic environment. Despite the presence of microbes and/or other contaminants in this environment, contamination of the fluid flow pathway between the drug-filled container 14 and the delivery member of the insertion mechanism 12 should not be a concern because the fluid flow pathway would have been previously sterilized and seal closed. Also, because there is not a risk of contamination of the fluid flow pathway, it may not be necessary to subject the drug delivery device 10 to a terminal sterilization treatment involving radiation beams, which could potentially damage the drug 32 stored in the container 14. Nevertheless, in some embodiments, the delivery device 10 may be subjected to a gaseous sterilization treatment at the completion of assembly.

Referring to FIGS. 2-7, set forth below is additional description of the carrier 110 and the sleeve 120, as well as alternative embodiments thereof. FIG. 2 is a cross-sectional view of the carrier 110 holding the insertion mechanism 12, the empty container 14, and the fluid pathway connection assembly 22 in alignment with each other. The carrier 110 may have a proximal end 112 and a distal end 114, and a longitudinal axis A3 passing centrally through the proximal end 112 and the distal end 114. In the illustrated embodiment, the carrier 110 aligns the insertion mechanism 12 and the container 14 such that the longitudinal axis A1 of the container 14, the longitudinal axis A2 of the cannula 23 of the insertion mechanism 12, and the longitudinal axis A3 of the carrier 110 are coaxial, and thus parallel, with each other. In alternative embodiments, the longitudinal axis A1 of the container 14 and/or the longitudinal axis A2 of the cannula 23 of the insertion mechanism 12 may be parallel to the longitudinal axis A3 of the carrier 110 and/or to each other, but the longitudinal axes A1-A3 may not necessarily be coaxial with each other.

The carrier 110 may have a generally cylindrical overall shape and a hollow interior 116. As shown in FIG. 2, the insertion mechanism 12 and the fluid pathway connection assembly may be entirely disposed within the hollow interior 116 of the carrier 110, and at least the distal end 37 of the container 14 may be disposed in the hollow interior 116 of the carrier 110. In alternative embodiments, a portion of the insertion mechanism 12 and/or the fluid pathway connection assembly 22 may protrude outside of the carrier 110.

Furthermore, the carrier 110 may have an inner circumferential surface 140 facing radially inwardly and surrounding the hollow interior 116, and an outer circumferential surface 142 facing radially outwardly. The carrier 110 may have a proximally facing end surface 144 and a distally facing end surface 146. Openings 148 and 149 may be formed in, respectively, the proximally facing end surface 144 and the distally facing end surface 146, and may each communicate with the hollow interior 116. As such, the hollow interior 116 and the openings 148 and 149 may define a central passage extending through the carrier 110 from the proximal end 112 to the distal end 114. The opening 149 may function as an access port that advantageously permits flow testing to be performed on the insertion mechanism 12 prior to removing the insertion mechanism 12 from the carrier 110.

Still referring to FIG. 2, the sleeve 120 may possess a proximal end 122 and a distal end 124, and a longitudinal axis A4 passing centrally through the proximal end 122 and the distal end 124. The parting line 121 may be disposed between the proximal end 122 and the distal end 124 of the sleeve 120. The longitudinal axis A4 of the sleeve 120 may be coaxial with and/or parallel to the longitudinal axis A1 of the container 14 when the proximal end 36 of the container 14 is received within a hollow interior 126 of the sleeve 120, as shown in FIG. 2. The sleeve 120 may have a generally cylindrical overall shape, and may be significantly longer than the carrier 110. Furthermore, the sleeve 120 may have an inner circumferential surface 150 facing radially inwardly and surrounding the hollow interior 126, and an outer circumferential surface 152 facing radially outwardly. The sleeve 120 may have a proximally facing end surface 154 and a distally facing end surface 156.

Openings 158 and 159 may be formed in, respectively, the proximally facing end surface 154 and the distally facing end surface 156 of the sleeve 120, and may each communicate with the hollow interior 126. As such, the hollow interior 126 and the openings 158 and 159 may define a central passage extending through the sleeve 120 from the proximal end 122 to the distal end 124.

In addition to receiving the container 14, the hollow interior 126 of the sleeve 120 may also receive the proximal end 112 of the carrier 110, as illustrated in FIG. 2. The distal end 124 of the sleeve 120 may surround and may be removably connected to the proximal end 112 of the carrier 110. In some embodiments, corresponding recesses and protrusions may be formed on the inner circumferential surface 150 of the distal end 124 of the sleeve 120 and the outer circumferential surface 142 of the proximal end 112 of the carrier 110 and may be configured to matingly engage each other to form a snap fit connection between the carrier 110 and the sleeve 120. In other embodiments, a interference type or press fit connection may exist between the carrier 110 and the sleeve 120.

The sleeve 120 may initially be formed as a single, unitary one-piece structure, with the proximal end 122 and the distal end 124 integrally formed with each other. As described above, during assembly, the sleeve 120 may be divided into two pieces at the parting line 121 by ripping, tearing, breaking, cutting, or otherwise physically separating the distal end 124 of the sleeve 120 from the proximal end 122 of the sleeve 120. In order to facilitate this breaking apart of the sleeve 120, the parting line 121 may have a wall thickness T1 that is less than the wall thickness T2 of the proximal end 122 of the sleeve 120 and/or less than the wall thickness T3 of the distal end 124 of the sleeve 120. Accordingly, the parting line 121 may be formed by a portion of the sleeve 120 having a reduced wall thickness relative to the proximal end 122 of the sleeve 120 and/or the distal end 124 of the sleeve 120. In some embodiments, the parting line 121 may be formed by a serrated portion of the wall of the sleeve 120. In some embodiments, to facilitate breaking at the parting line 121, the sleeve 120 may be constructed of a material that is more brittle than a material used to construct the carrier 110.

In alternative embodiments, the parting line 121 may be formed by one or more interlocking hooks and depressions formed at opposing ends of the proximal end 122 of the sleeve 120 and the distal end 124 of the sleeve 120. In such alternative embodiments, the proximal end 122 of the sleeve 120 and the distal end 124 of the sleeve 120 may be separate structures which are not torn away from each other but rather unlocked from each other during the assembly process.

In some embodiments, an outer diameter D1 of the carrier 110 may be equal to or substantially equal to an outer diameter D2 of the sleeve 120. In some embodiments, the carrier 110 and/or the sleeve 120 may have a constant outer diameter along its entire length; whereas in other embodiments, the carrier 110 and/or the sleeve 120 may have an outer diameter that varies slightly along its length. In such latter embodiments, a maximum outer diameter of the carrier 110 may be equal to or less than a maximum outer diameter of the sleeve 120.

Turning to FIGS. 3-6, illustrated is another version of the fill-finish assembly. Elements of the fill-finish assembly 330 shown in FIGS. 3-6 which are the same as or similar to elements of the fill-finish assembly 130 are designated by the same reference numeral, incremented by 200. A description of many of these elements is abbreviated or even eliminated in the interest of brevity.

Figure 3:
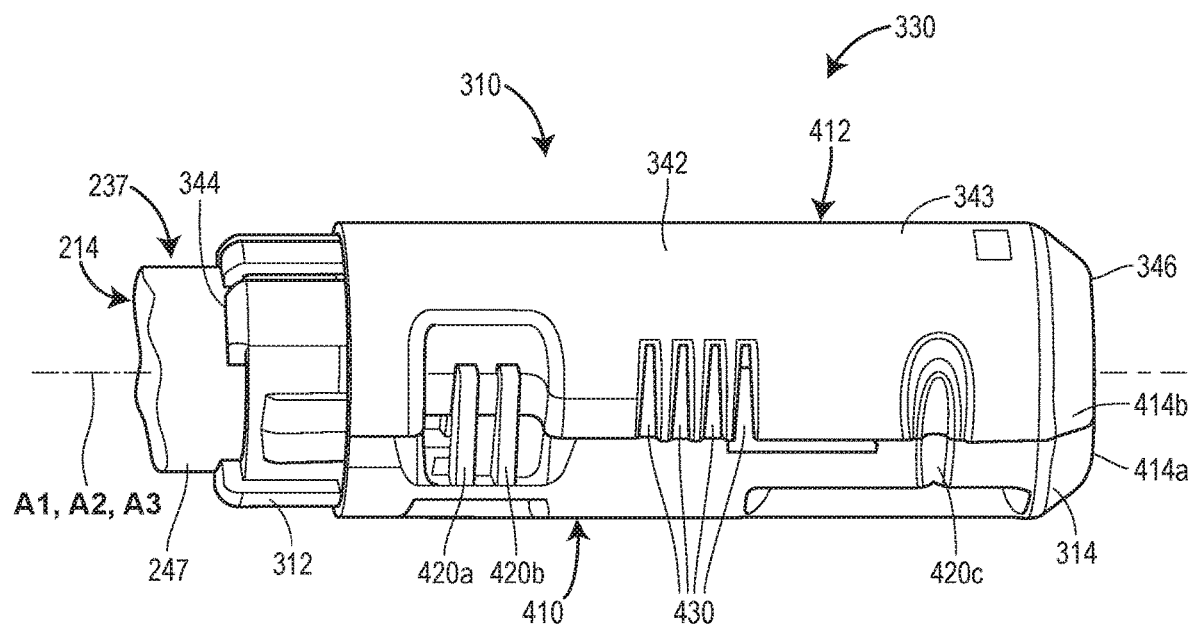
FIG. 3 illustrates a perspective side view of another embodiment of a fill-finish assembly in accordance with principles of the present disclosure.
Figure 4:
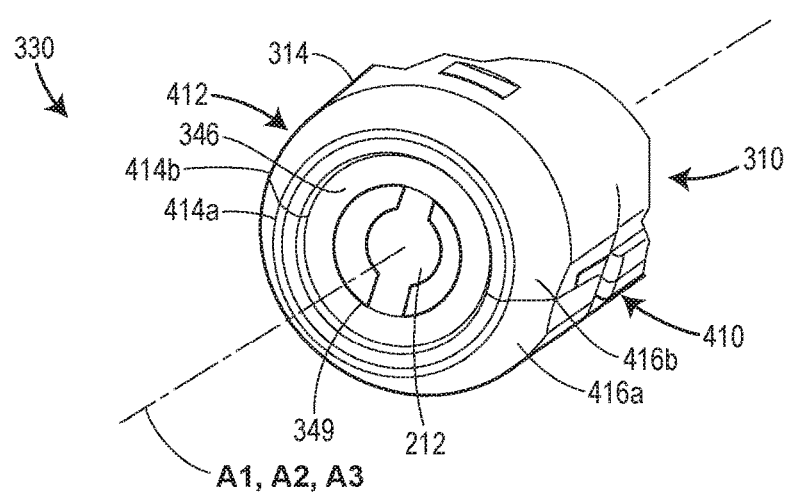
FIG. 4 depicts another perspective view of a distal end of the fill-finish assembly shown FIG. 3.

Referring to FIGS. 3 and 4, the carrier 310 may include a first collar section 410 and a second collar section 412, each of which may generally have a C-shaped cross-section. The first collar section 410 may have a first end 414a and a second end 416a defining opposite ends of its C-shaped cross-section. Similarly, the second collar section 412 may have a first end 414b and a second end 416b defining opposite ends of its C-shaped cross-section. The first end 414a of the first collar section 410 may be arranged in opposition to and/or directly contact the first end 414b of the second collar section 412; and the second end 416a of the first collar section 410 may be arranged in opposition to and/or directly contact the second end 416b of the second collar section 412. Furthermore, the first end 414a of the first collar section 410 may be removably connected to the first end 414b of the second collar section 412; and the second end 416a of the first collar section 410 may be removably connected to the second end 416b of the second collar section 412. When connected together, the first collar section 410 and the second collar section 412 may define the hollow interior 116 of the carrier 110. Furthermore, when the first and second collar sections 410 and 412 are connected together, an inner surface of the first collar section 410 and an inner surface of the second collar section 412 may form the inner circumferential surface 150 of the carrier 110, and an outer surface of the first collar section 410 and an outer surface of the second collar section 412 may form the outer circumferential surface 152 of the carrier 110.

Figure 5:
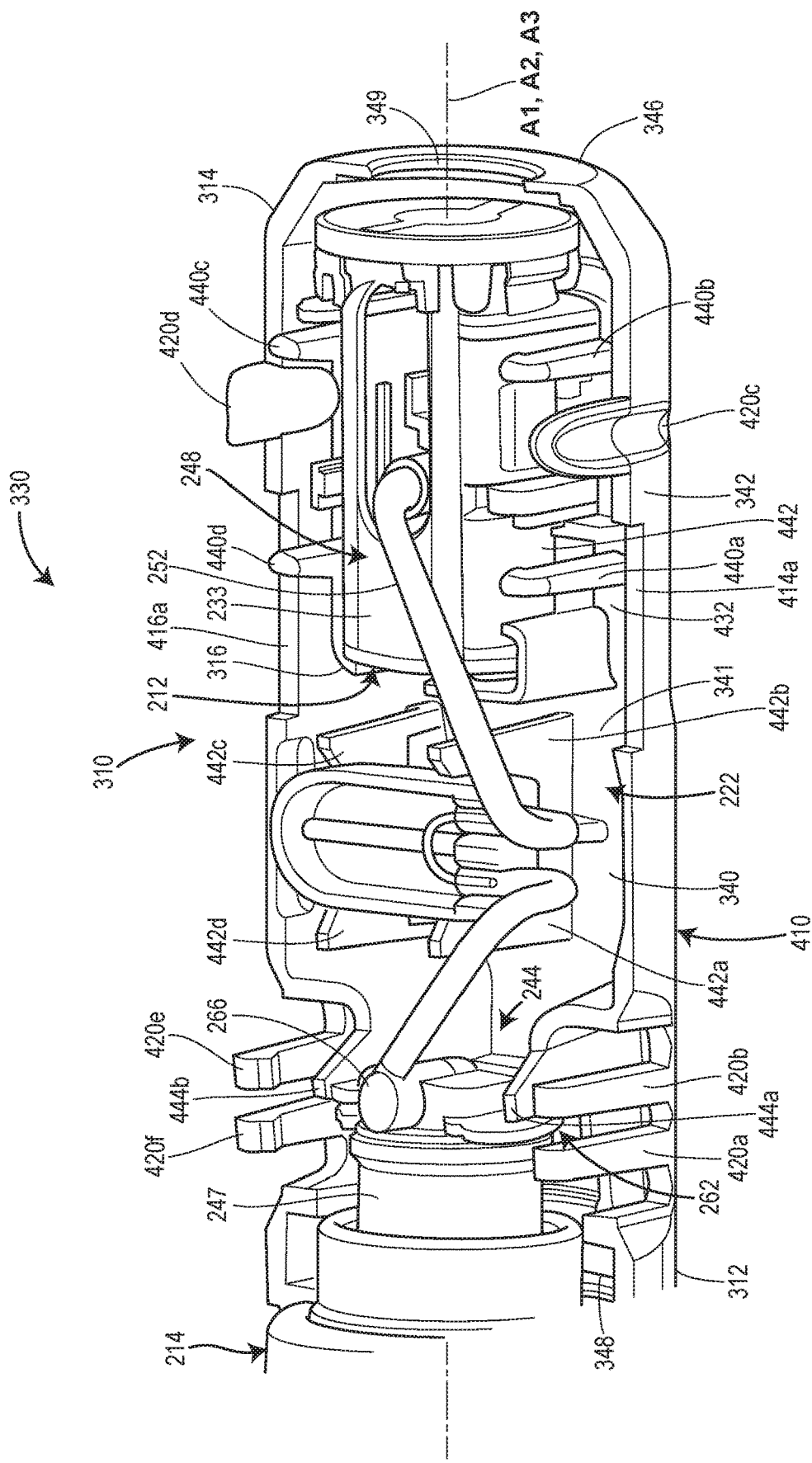
FIG. 5 illustrates a perspective view of the fill-finish assembly shown FIG. 3, with a collar section of a carrier being hidden to reveal an interior of the carrier.

As illustrated in FIGS. 3 and 5, a plurality of hooks or tabs 420a-f may extend from the first end 414a and/or the second end 416a of the first collar section 410 and may be configured to removably connect the first collar section 410 to the second collar section 412. In some embodiments, the second collar section 412 may include corresponding grooves or other structures for receiving and interlocking with each of the plurality of hooks or tabs 420a-f. The plurality of hooks or tabs 420a-f may form a snap fit or other frictional connection between the first collar section 410 and the second collar section 412 to resist separation of the first collar section 410 and the second collar section 412 after they have been connected. Mounting all of the hooks or tabs 420a-f on the first collar section 410 may, in certain cases, facilitate detachment of the first collar section 410 from the second collar section 412 after fill-finish processing is complete. Nevertheless, in alternative embodiments, some or all of the plurality of hooks or tabs 420a-f may extend from the second collar section 412.

As depicted in FIGS. 3 and 5, each of the plurality of hooks or tabs 420a-f may extend in a direction which is perpendicular or non-parallel to the longitudinal axis A3 of the carrier 310 and toward either the opposing first end 414b or the opposing second end 416b of the second collar section 412. Furthermore, in some embodiments, the plurality of hooks or tabs 420a-f may be integrally formed as a single unitary structure with the first collar section 410, as shown in FIGS. 3 and 5.

Referring to FIG. 3, one or more openings 430 may be formed in an outer surface 343 of the second collar section 412 and may communicate with the hollow interior 316. The opening(s) 430 may be aligned with at least a portion of the fluid pathway connection assembly 222, such that the opening(s) 430 are arranged at a similar axial position along the longitudinal axis A3 as the at least a portion of the fluid pathway connection assembly 222. The opening(s) 430 may allow robotic finger(s) or other positioning member(s) to be temporarily inserted into the second collar section 412 and displace or otherwise engage the flexible tubing 252 of the fluid pathway connection assembly 222 while the second collar section 412 is removably connected to the first collar section 410. Such positioning member(s) may help maintain spacing between the flexible tubing 252 and the first collar section 410 and/or the second collar section 412, such that the flexible tubing 252 is not pinched between the first collar section 410 and the second collar section 412. After the first collar section 410 and the second collar section 412 have been removably connected to each other, the positioning member(s) may be withdrawn from the second collar section 412 through the opening(s) 430.

Referring to FIG. 4, the opening 349 may be formed in the distally facing end surface 346 of the carrier 310, and the longitudinal axis A3 may pass centrally through the opening 349. The opening 349 may communicate with the hollow interior 316 of the carrier 310 and provide access to the distal end of the insertion mechanism 12 when the insertion mechanism 212 is disposed within the carrier 310. As such, the opening 349 advantageously may permit flow testing to be performed on the insertion mechanism 212 prior to removing the insertion mechanism 212 from the carrier 310. Such flow testing may help identify any occlusions or leaks prior to installation of the insertion mechanism 212 in the drug delivery device 10.

Figure 6:
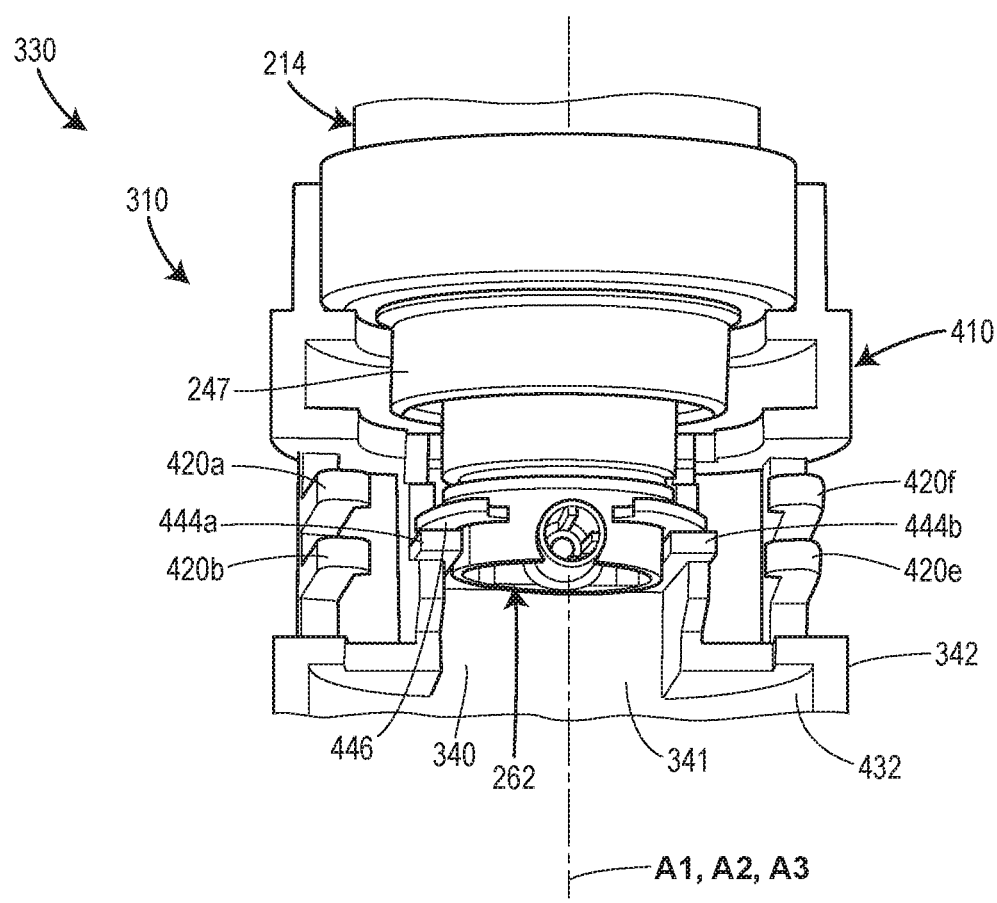
FIG. 6 is an enlarged perspective view of a distal end of container shown in FIG. 5.

With reference to FIGS. 5 and 6, features for mounting or securing the insertion mechanism 212, the container 214, and/or the fluid pathway connection mechanism 222 within the carrier 310 will now be described. In general, the carrier 310 may be configured to limit (e.g., inhibit or prevent) axial and/or rotational movement of the insertion mechanism 212, the container 214, and/or the fluid pathway connection mechanism 222 relative to each other and/or the carrier 310. By restraining movement of the insertion mechanism 212, the container 214, and/or the fluid pathway connection mechanism 222, the below-described gripping elements incorporated into the first collar section 410 may reduce the possibility of the insertion mechanism 212, the container 214, and/or the fluid pathway connection mechanism 222 becoming dislodged during spinning and other inertial maneuvers to which the fill-finish assembly 330 may be subjected during fill-finish processing and/or other handling. In some embodiments, such as the one illustrated in FIGS. 5 and 6, the first collar section 410 of the carrier 310 may be configured to limit axial and/or rotational movement of the insertion mechanism 212, the container 214, and the fluid pathway connection mechanism 222 independently of the second collar section 412. Accordingly, the first collar section 410 may secure the insertion mechanism 212, the container 214, and the fluid pathway connection mechanism 222 without assistance from the second collar section 412. This may simplify the process of mounting the insertion mechanism 212, the container 214, and the fluid pathway connection mechanism 222 within the carrier 310. For instance, each of the insertion mechanism 212, the container 214, and the fluid pathway connection mechanism 222 may be inserted through an opening 432 defined between the first end 414a and the second end 416a of the first collar section 410 in a direction that is perpendicular or substantially perpendicular to the longitudinal axis A3. Accordingly, top-down assembly and/or disassembly of the insertion mechanism 212, the container 214, and the fluid pathway connection mechanism 222 within the first collar section 410 may be feasible.

FIG. 5 illustrates that the insertion mechanism 212 may be nested within and/or secured by a plurality of ribs or protrusions 440a-d extending inwardly from an inner surface 341 of the first collar section 410. Each of the protrusions 440a-d may directly contact and frictionally engage or otherwise grip an outer circumferential surface 442 of the insertion mechanism housing 233 to limit axial and/or rotational movement of the insertion mechanism 212 relative to the first collar section 410. Each of the protrusions 440a-d may extend inwardly from the inner surface 341 of the first collar section 410 along a direction which emanates radially from or is otherwise perpendicular to the longitudinal axis A3. Furthermore, in some embodiments, each of the protrusions 440a-d may include a hook or other gripping element that interlocks with a corresponding groove or other structure on the insertion mechanism housing 233.

Similarly, FIG. 5 shows that the fluid pathway connection assembly 222 may be nested within and/or secured by a plurality of ribs or protrusions 442a-d extending inwardly from the inner surface 341 of the first collar section 410. Each of the protrusions 442a-d may directly contact and frictionally engage or otherwise grip a portion of the fluid pathway connection assembly 222 to limit axial and/or rotational movement of the fluid pathway connection assembly 222 relative to the first collar section 410. Each of the protrusions 442a-d may extend inwardly from the inner surface 341 of the first collar section 410 along a direction which emanates radially from or is otherwise perpendicular to the longitudinal axis A3. Furthermore, in some embodiments, each of the protrusions 442a-d may include a hook or other gripping element that interlocks with a corresponding groove or other structure on the fluid pathway connection assembly 222. Furthermore, as shown in FIG. 5, the protrusions 442a-d may not directly contact the flexible tubing 352 of the fluid pathway connection assembly 222.

With continued reference to FIG. 5, and now also FIG. 6, the container 14 may be nested within and/or secured by a plurality of ribs or protrusions 444a and 444b extending inwardly from the inner surface 341 of the first collar section 410. Each of the protrusions 444a and 444b may directly contact and frictionally engage or otherwise grip a portion of the container 14, including, e.g., its seal assembly, to limit axial and/or rotational movement of the container 14 relative to the first collar section 410. Furthermore, in some embodiments, each of the protrusions 444a and 444b may directly contact and frictionally engage a distally facing end surface 446 of the container 14, as seen in FIG. 6. Each of the protrusions 444a and 444b may extend inwardly from the inner surface 341 of the first collar section 410 along a direction which emanates radially from or is otherwise perpendicular to the longitudinal axis A3. Furthermore, in some embodiments, each of the protrusions 444a and 444b may include a hook or other gripping element that interlocks with a corresponding groove or other structure on the container 14.

Furthermore, in some embodiments, any one of or any combination of the protrusions 440a-d, 442a-d, 444a, and 444b may be integrally formed as a single unitary structure with the first collar section 410.

Although the fill-finish assembly 330 shown in FIGS. 3-6 does not include a sleeve, in some embodiments a sleeve similar to the sleeve 120 shown in FIG. 2 may be incorporated into the fill-finish assembly 330.

Figure 7:
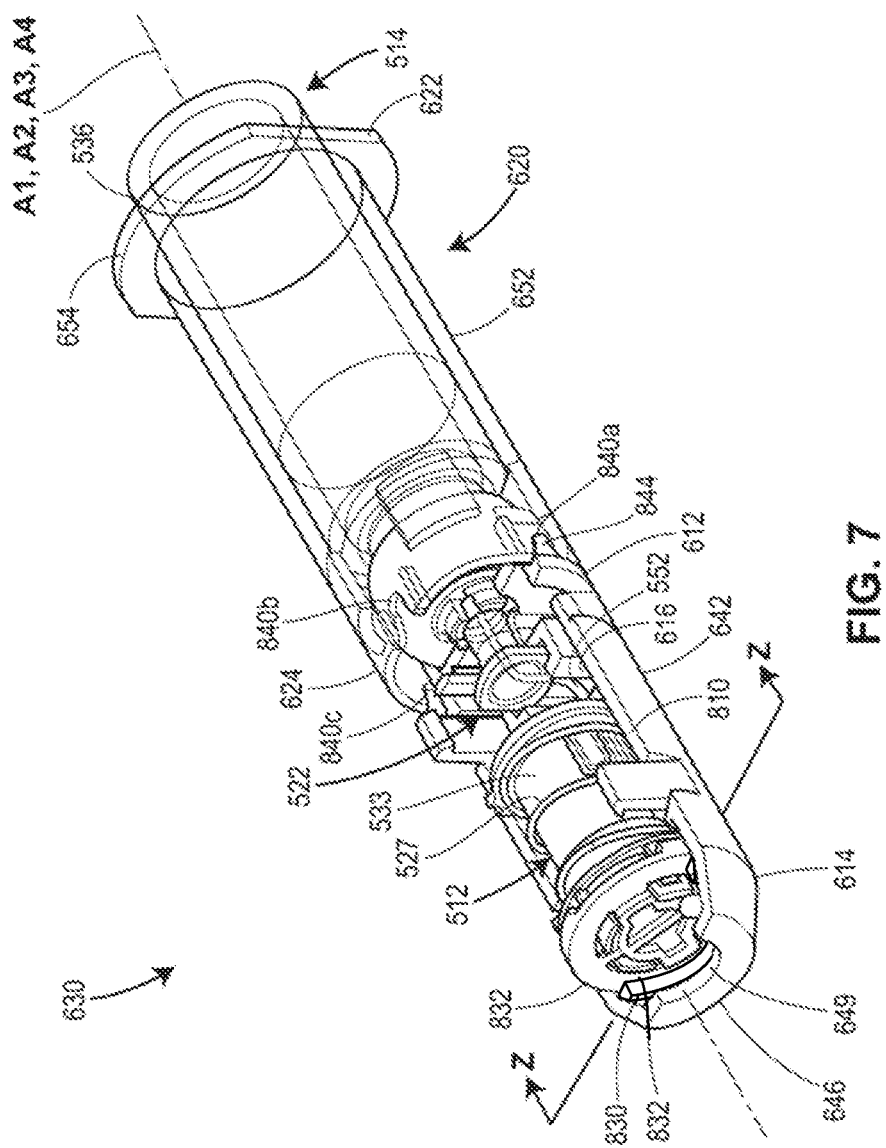
FIG. 7 illustrates a perspective side view of another embodiment of a fill-finish assembly in accordance with principles of the present disclosure, with a collar section of a carrier being hidden to reveal an interior of the carrier.
Figure 8:
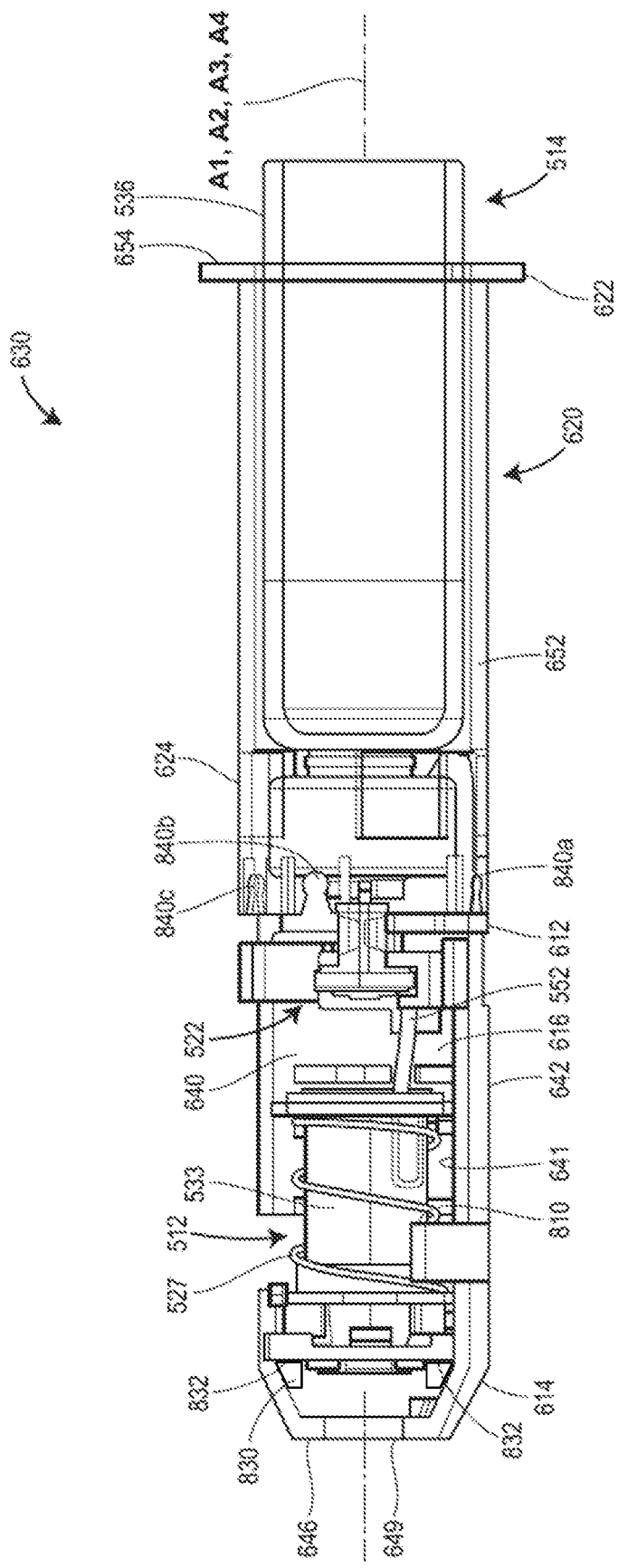
FIG. 8 is a top plan view of the fill-finish assembly shown in FIG. 7.
Figure 9:
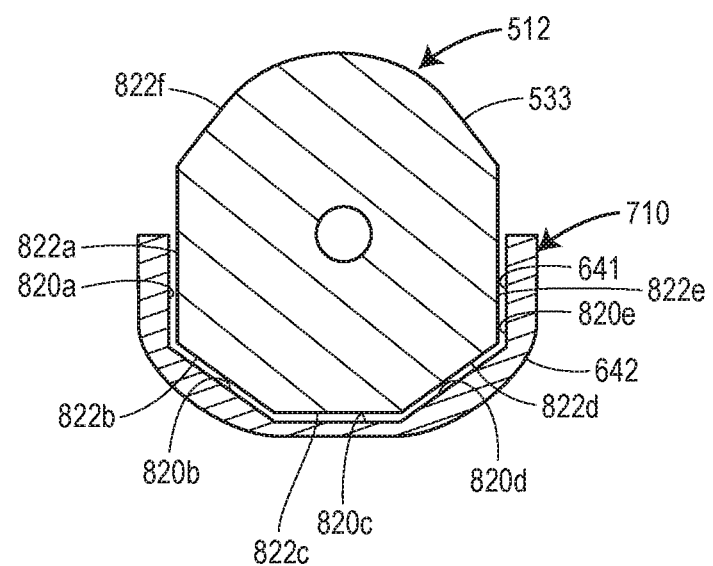
FIG. 9 is a cross-sectional view along line Z-Z in FIG. 7.

Turning to FIGS. 7-9 illustrated is yet another version of the fill-finish assembly. Elements of the fill-finish assembly 530 shown in FIGS. 7-9 which are the same as or similar to elements of the fill-finish assembly 330 are designated by the same reference numeral, incremented by 300. A description of many of these elements is abbreviated or even eliminated in the interest of brevity.

In the embodiment shown in FIG. 5, multiple protrusions extending from the first collar section engage the outer circumferential surface of the insertion mechanism housing in order to secure the insertion mechanism 12. By contrast, in the embodiment shown in FIG. 7, a single rib or protrusion 810 extends inwardly from the inner surface 641 of the first collar section 710 to directly contact and frictionally engage or otherwise grip an outer circumferential surface 742 of the insertion mechanism housing 533 to limit axial and/or rotational movement of the insertion mechanism 512 relative to the first collar section 710. Thus, in some embodiments, contact between the carrier 610 and the outer circumferential surface 742 of the insertion mechanism housing 533 may be limited to the protrusion 810. The protrusion 810 may extend inwardly from the inner surface 641 of the first collar section 710 along a direction which emanates radially from or is otherwise perpendicular to the longitudinal axis A3. Depending on the configuration of the flexible tubing 552 of the fluid pathway connection assembly 522, a single protrusion 810 may be preferred so as to reduce the possibility of the flexible tubing 552 being snagged or pinched by the protrusion 810 when securing the insertion mechanism 512 within the first collar section 710.

Referring to FIGS. 7 and 9, the inner surface 641 of the first collar section 710 may include a plurality of planar portions 820a-e, also referred to as flats, and the outer circumferential surface 742 of the insertion mechanism housing 533 may include a plurality of planar portions 822a-f. Each of the planar portions 820a-e may engage a respective one of the planar portions 822a-e in order to limit rotation of the insertion mechanism 512 relative to the first collar section 710. The planar portion 822f may engage a planar portion of the second collar section (not illustrated) to provide a similar effect.

Referring to FIGS. 7 and 8, a protrusion 830 may extend inwardly from the inner surface 641 of the first collar section 710 and engage a distally facing end surface 832 of the insertion mechanism 512 to limit axial movement of the insertion mechanism 512 relative to the first collar section 710. The protrusion 830 may extend inwardly from the inner surface 641 of the first collar section 710 along a direction which emanates radially from or is otherwise perpendicular to the longitudinal axis A3.

Still referring to FIGS. 7 and 8, a plurality of openings 840a-c may be formed in an outer circumferential surface 652 of the sleeve 620 at the distal end 624 of the sleeve 620 and at least one corresponding protrusion 844 may extend in a proximal direction from the proximal end 612 of the carrier 610. The protrusion 844 may be received in the opening 840a to create a snap-fit connection between the carrier 610 to the sleeve 620. This snap-fit connection may facilitate removal of the sleeve 620 from the carrier 610 after fill-finish processing has been completed. In some embodiments, such as the one shown in FIGS. 7 and 8, at least a portion of the openings 840a-c may possess a triangular cross-section, in order to facilitate bump off of the sleeve 620 from the carrier 610 during disassembly.

Drug Information

The above description describes various assemblies, devices, and methods for use with a drug delivery device. It should be clear that the assemblies, drug delivery devices, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of sequence identification number 2 as set forth therein in FIG. 2 and/or the heavy chain of sequence identification number 4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of sequence identification numbers 305-351, including TN8-19-1 through TN8-19-40, TN8-19 con1 and TN8-19 con2; peptibodies of the mL2 family of sequence identification numbers 357-383; the mL15 family of sequence identification numbers 384-409; the mL17 family of sequence identification numbers 410-438; the mL20 family of sequence identification numbers 439-446; the mL21 family of sequence identification numbers 447-452; the mL24 family of sequence identification numbers 453-454; and those of sequence identification numbers 615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1(N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H 33, L34H34, L35H35, L36H36, L37H37, L38H38, L39H39, L40H40, L41H41, L42H42, L43H43, L44H44, L45H45, L46H46, L47H 47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (K), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences designated therein as, respectively, sequence identification number 1 and sequence identification number 7); 5D (having light chain variable and heavy chain variable sequences designated therein as, respectively, sequence identification number 2 and sequence identification number 9); 2H (having light chain variable and heavy chain variable sequences designated therein as, respectively, sequence identification number 3 and sequence identification number 10); 43H (having light chain variable and heavy chain variable sequences designated therein as, respectively, sequence identification number 6 and sequence identification number 14); 41H (having light chain variable and heavy chain variable sequences designated therein as, respectively, sequence identification number 5 and sequence identification number 13); and 15H (having light chain variable and heavy chain variable sequences designated therein as, respectively, sequence identification number 4 and sequence identification number 12), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of sequence identification number 17 and the light chain of sequence identification number 18; those having the heavy chain variable region of sequence identification number 6 and the light chain variable region of sequence identification number 8; those having the heavy chain of sequence identification number 19 and the light chain of sequence identification number 20; those having the heavy chain variable region of sequence identification number 10 and the light chain variable region of sequence identification number 12; those having the heavy chain of sequence identification number 32 and the light chain of sequence identification number 20; those having the heavy chain variable region of sequence identification number 30 and the light chain variable region of sequence identification number 12; those having the heavy chain sequence of sequence identification number 21 and the light chain sequence of sequence identification number 22; those having the heavy chain variable region of sequence identification number 14 and the light chain variable region of sequence identification number 16; those having the heavy chain of sequence identification number 21 and the light chain of sequence identification number 33; and those having the heavy chain variable region of sequence identification number 14 and the light chain variable region of sequence identification number 31, as disclosed in the foregoing publication. A specific antibody contemplated is antibody 1119 as disclosed in the foregoing U.S. publication and having a complete heavy chain of sequence identification number 17 as disclosed therein and having a complete light chain of sequence identification number 18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising sequence identification number 8 and a light chain variable region having sequence identification number 6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/ILia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT- 213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BITE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery devices, methods, and components thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, components described herein with reference to certain kinds of drug delivery devices, such as on-body injector drug delivery devices or other kinds of drug delivery devices, can also be utilized in other kinds of drug delivery devices, such as autoinjector drug delivery devices.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A fill-finish assembly comprising:
 a container;
 an insertion mechanism including a delivery member and an insertion mechanism housing, the insertion mechanism being configured to move the delivery member from a retracted position wherein the delivery member is withdrawn inside the insertion mechanism housing to a deployed position wherein at least a portion of the delivery member extends outside of the insertion mechanism housing;
 a fluid pathway connection assembly disposed between the container and the insertion mechanism, the fluid pathway connection assembly being selectively activatable to establish fluid communication between the container and the delivery member;
 a carrier having a hollow interior containing at least a portion of each of the container, the insertion mechanism, and the fluid pathway connection assembly, the carrier being configured to hold the container, the insertion mechanism, and the fluid pathway connection assembly in alignment with each other to limit axial and rotational movement of the container, the insertion mechanism, and the fluid pathway connection assembly relative to each other; and a protrusion extending inwardly from an inner circumferential surface of the carrier and directly engaging a distally facing end surface of the insertion mechanism to limit axial movement of the insertion mechanism relative to the carrier.

2. The fill-finish assembly of claim 1, the carrier having a proximal end receiving at least a portion of the container, a distal end receiving at least a portion of the insertion mechanism, and a longitudinal axis passing centrally through the proximal end and the distal end.

3. The fill-finish assembly of claim 2, the delivery member having a longitudinal axis arranged parallel to the longitudinal axis of the carrier, and the container having a longitudinal axis arranged parallel to the longitudinal axis of the carrier.

4. The fill-finish assembly of claim 1, the carrier including a first collar section and a second collar section, each one of the first collar section and the second collar section having a first end and a second end removably connected to, respectively, the first end and the second end of the other one of the first collar section and the second collar section to define the hollow interior of the carrier.

5. The fill-finish assembly of claim 4, the first collar section being configured to hold the insertion mechanism, the fluid pathway connection assembly, and the container in alignment with each other independently of the second collar section.

6. The fill-finish assembly of claim 1, the carrier being configured to limit axial and rotational movement of the insertion mechanism, the fluid pathway connection assembly, and the container relative to each other, the fill-finish assembly further comprising one or more of (i) through (iv):
  (i) a first protrusion extending inwardly from an inner circumferential surface of the carrier and engaging at least one of the fluid pathway connection assembly or the container to limit rotational movement of the at least one of the fluid pathway connection assembly or the container relative to the carrier,
  (ii) a third protrusion extending inwardly from an inner circumferential surface of the carrier and engaging an outer circumferential surface of the insertion mechanism housing, wherein contact between the carrier and the outer circumferential surface of the insertion mechanism housing is limited to the third protrusion, and
  (iii) the carrier having an inner circumferential surface and the insertion mechanism housing having an outer circumferential surface, each of the inner circumferential surface of the carrier and the outer circumferential surface of the insertion mechanism housing having a planar portion, wherein the planar portion of the inner circumferential surface of the carrier engages the planar portion of the outer circumferential surface of the insertion mechanism housing to limit rotational movement of the insertion mechanism housing relative to the carrier.

7. The fill-finish assembly of claim 1, comprising one or more of (i) through (v):
  (i) a first opening formed in a distally facing end surface of the carrier and communicating with the hollow interior,
  (ii) the insertion mechanism, the fluid pathway connection assembly, and the container defining a sterilized fluid flow pathway,
  (iii) the carrier having an outer circumferential surface, at least a portion of the outer circumferential surface being substantially cylindrical,
  (iv) a sleeve having a proximal end, a distal end, and a hollow interior, the distal end of the sleeve being removably connected to a proximal end carrier, the container being at least partially disposed in the hollow interior of the sleeve, and
  (v) the container having a proximal end with an opening and a distal end removably connected to the carrier.

8. The fill-finish assembly of claim 1, wherein the carrier comprises a first collar section removably coupled with a second collar section, wherein the first collar section, independent of being coupled with the second collar section, is configured to at least selectively prevent the insertion mechanism and the fluid pathway connection assembly from rotating relative to each other.

9. A fill-finish assembly comprising:
  a container;
  an insertion mechanism including a delivery member and an insertion mechanism housing, the insertion mechanism being configured to move the delivery member from a retracted position wherein the delivery member is withdrawn inside the insertion mechanism housing to a deployed position wherein at least a portion of the delivery member extends outside of the insertion mechanism housing;
  a fluid pathway connection assembly disposed between the container and the insertion mechanism, the fluid pathway connection assembly being selectively activatable to establish fluid communication between the container and the delivery member;
  a carrier having a hollow interior containing at least a portion of each of the container, the insertion mechanism, and the fluid pathway connection assembly, the carrier being configured to hold the container, the insertion mechanism, and the fluid pathway connection assembly in alignment with each other to limit axial and rotational movement of the container, the insertion mechanism, and the fluid pathway connection assembly relative to each other;
  a protrusion extending inwardly from an inner circumferential surface of the carrier and directly engaging a distally facing end surface of the insertion mechanism to limit axial movement of the insertion mechanism relative to the carrier; and
  one or more of (i) through (v):
    (i) a first opening formed in a distally facing end surface of the carrier and communicating with the hollow interior,
    (ii) the insertion mechanism, the fluid pathway connection assembly, and the container defining a sterilized fluid flow pathway,
    (iii) the carrier having an outer circumferential surface, at least a portion of the outer circumferential surface being substantially cylindrical,
    (iv) a sleeve having a proximal end, a distal end, and a hollow interior, the distal end of the sleeve being removably connected to a proximal end carrier, the container being at least partially disposed in the hollow interior of the sleeve, and
    (v) the container having a proximal end with an opening and a distal end removably connected to the carrier.

* * * * *